(12) United States Patent
Ryan (10) Patent No.: US 9,254,372 B2
(45) Date of Patent: Feb. 9, 2016

(54) CATHETER ASSEMBLY WITH DEFLECTION SIZE ADJUSTABILITY

(75) Inventor: Garrett Ryan, Surry Hills (AU)

(73) Assignee: CathRX LTD, Homebush Bay (AU)

( * ) Notice: Subject to any disclaimer, the term of this patent is extended or adjusted under 35 U.S.C. 154(b) by 230 days.

(21) Appl. No.: 13/816,711

(22) PCT Filed: Aug. 12, 2011

(86) PCT No.: PCT/AU2011/001021
§ 371 (c)(1),
(2), (4) Date: Feb. 12, 2013

(87) PCT Pub. No.: WO2012/019232
PCT Pub. Date: Feb. 16, 2012

(65) Prior Publication Data
US 2013/0144209 A1 Jun. 6, 2013

Related U.S. Application Data

(60) Provisional application No. 61/373,717, filed on Aug. 13, 2010.

(51) Int. Cl.
*A61M 37/00* (2006.01)
*A61M 25/01* (2006.01)

(52) U.S. Cl.
CPC ....... *A61M 25/0147* (2013.01); *A61M 25/0133* (2013.01); *A61M 25/0136* (2013.01); *A61M 2025/015* (2013.01)

(58) Field of Classification Search
CPC .................... A61M 25/0136; A61M 2025/015
USPC .............. 604/95.01, 95.04, 165.04, 264, 528; 606/108; 623/1.11
See application file for complete search history.

(56) References Cited

U.S. PATENT DOCUMENTS

| | | | |
|---|---|---|---|
| 5,545,200 A | 8/1996 | West et al. | |
| 5,987,344 A | 11/1999 | West et al. | |
| 6,554,794 B1* | 4/2003 | Mueller et al. | 604/95.04 |
| 2005/0060016 A1* | 3/2005 | Wu et al. | 623/1.11 |
| 2006/0252993 A1* | 11/2006 | Freed | A61B 1/0125 600/146 |
| 2007/0112409 A1* | 5/2007 | Wu et al. | 623/1.12 |

(Continued)

FOREIGN PATENT DOCUMENTS

| | | |
|---|---|---|
| EP | 0982047 A2 | 3/2000 |
| EP | 0985423 | 3/2000 |

(Continued)

OTHER PUBLICATIONS

Search Report of International Application No. PCT/AU2011/001021, mailed Oct. 20, 2011, 3 pages.

(Continued)

*Primary Examiner* — Nicholas Lucchesi
*Assistant Examiner* — Gerald Landry, II
(74) *Attorney, Agent, or Firm* — TraskBritt (57) ABSTRACT

A catheter includes a handle, a catheter sheath and a stylet received within a lumen of the catheter sheath. A carrier arrangement projects from the distal end of the handle, the carrier arrangement mounting the catheter sheath and at least part of the deflection stylet. The catheter handle includes an adjustment unit having a gear mechanism that controls at least one of the deflection of the distal part of the stylet and the extent of deflection of the distal part of the stylet.

18 Claims, 3 Drawing Sheets

(56) References Cited

U.S. PATENT DOCUMENTS

| | | | |
|---|---|---|---|
| 2007/0156116 A1* | 7/2007 | Gonzalez | 604/528 |
| 2007/0225641 A1 | 9/2007 | Schneider et al. | |
| 2009/0105638 A1* | 4/2009 | Partlett et al. | 604/95.01 |
| 2011/0054287 A1* | 3/2011 | Schultz | A61B 5/0422 600/374 |
| 2011/0166455 A1* | 7/2011 | Cully | A61B 8/12 600/463 |

FOREIGN PATENT DOCUMENTS

| | | |
|---|---|---|
| EP | 1050316 B1 | 12/2003 |
| WO | 96/34653 | 11/1996 |
| WO | WO 96/37252 | 11/1996 |
| WO | WO 00/67834 | 11/2000 |
| WO | WO 01/68178 | 9/2001 |
| WO | WO 2007/002713 | 1/2007 |

OTHER PUBLICATIONS

Written Opinion of International Application No. PCT/AU2011/001021, mailed Oct. 20, 2011, 7 pages.

European Search Report for EP Application No. 11 815 908.6, dated Dec. 20, 2013, 3 pages.

European Examination Report for EP Application No. 11 815 908.6, dated Feb. 18, 2014, 6 pages.

* cited by examiner

CATHETER ASSEMBLY WITH DEFLECTION SIZE ADJUSTABILITY

CROSS-REFERENCE TO RELATED APPLICATIONS

This application is a national phase entry under 35 U.S.C. § 371 of International Patent Application PCT/AU2011/001021, filed Aug. 12, 2011, designating the United States of America and published in English as International Patent Publication WO 2012/019232 A1 on Feb. 16, 2012, which claims the benefit under Article 8 of the Patent Cooperation Treaty and under 35 U.S.C. § 119(e) to U.S. Provisional patent application Ser. No. 61/373,717, filed Aug. 13, 2010, the disclosure of each of which is hereby incorporated herein by this reference in its entirety.

TECHNICAL FIELD

This disclosure relates, generally, to a catheter and, more particularly, to a catheter handle assembly and to a catheter assembly including the catheter handle assembly.

BACKGROUND

Any discussion of the prior art throughout the specification should in no way be considered as an admission that such prior art is widely known or forms part of common general knowledge in the field.

In the field of cardiac procedures, use is made of a catheter that is steered through a patient's vasculature and is then placed at the desired site. Generally, the site is within a heart of the patient and a distal part of the catheter needs to be maneuvered into position against heart wall tissue. To be able to manipulate the distal part of the catheter to place it in tissue contact, the end of the catheter is flexible and steerable. A deflectable stylet is associated with the catheter for deflecting the distal part of the catheter.

Often, the part of the heart wall that needs to be accessed is awkwardly situated resulting in it being difficult to place the distal part of the catheter in contact with the desired part of the tissue to be treated or diagnosed.

BRIEF SUMMARY

It is an object of the present invention to overcome or ameliorate at least one of the disadvantages of the prior art, or to provide a useful alternative.

In one aspect, there is provided a catheter handle assembly that includes:

- a handle body having a proximal end and a distal end with a passage extending between the proximal end and the distal end of the handle body;
- a carrier arrangement projecting from the distal end of the handle body, the carrier arrangement mounting a catheter sheath and at least a part of a deflection stylet of a catheter, in use; and
- an adjustment unit arranged in the handle body and interposed between the handle body and the carrier arrangement, the adjustment unit comprising a gear mechanism that acts on the deflection stylet for adjusting at least one of deflection of a distal part of the stylet and the extent of deflection of the distal part of the stylet.

By "the extent of deflection of the distal part of the stylet" is meant the size of the radius of curvature of the deflected distal part of the deflectable member. However, the stylet may be able to be deflected in ways other than into a curved shape, for example, into a helical shape and the adjustment unit may be operable to adjust the shape of such helical deflection and the terminology "the extent of deflection of the distal part of the stylet" is intended to cover such applications as well as other applications.

The adjustment unit may be configured to adjust both deflection and the size of the deflection of the distal part of the stylet.

The carrier arrangement may comprise a deflection unit and a size selector unit. The deflection unit and the size selector unit may be operable substantially independently of each other.

The deflection unit may comprise a first tube and the size selector unit may comprise a second tube with the tubes being telescopically arranged with respect to each other and with respect to the distal end of the handle body. Each of the first tube and the second tube may carry a control knob at, or proximate, its distal end for effecting axial displacement of the first tube and the second tube relative to each other and relative to the distal end of the handle body.

The gear mechanism may comprise a first drive gear element carried by the first tube and a second drive gear element carried by the second tube, the gear mechanism further including a first driven gear assembly arranged in the handle body to be driven by the first drive gear element to effect deflection of the distal part of the stylet and a second driven gear assembly arranged in the handle body to be driven by the second gear element to effect selection of the size of the deflection of the stylet.

Each of the first drive gear element and the second drive gear element may comprise a rack. Each rack may project proximally from a proximal end of its associated tube. Further, each driven gear assembly may comprise a driven gear, in the form of a pinion, and a secondary rack. Each secondary rack may carry a mounting formation for removably mounting a part of the stylet. Thus, for reprocessing of the catheter, the stylet is able to be removed for refurbishment, sterilization, and/or replacement. Similarly, the catheter sheath is removably mounted to the handle to enable it to be reprocessed or replaced.

The driven gear of the first driven gear assembly may be located inwardly of ends of its associated rack when the distal part of the stylet is in a non-deflected condition, in use, so that bidirectional deflection of the distal part of the stylet is able to be effected by appropriate manipulation of the deflection unit.

The handle body may comprise a number of parts that are mated together to form the handle body, the parts being separable from each other to enable access to be gained to an interior of the handle body for reprocessing purposes.

In a second aspect, there is provided a catheter assembly that includes:

- a catheter handle assembly as described above;
- a catheter sheath extending from the distal end of the handle body, the catheter sheath defining at least one lumen; and
- a deflection stylet extending from the handle body and received in the at least one lumen of the catheter sheath.

BRIEF DESCRIPTION OF THE DRAWINGS

Preferred embodiments of the invention will now be described, by way of example only, with reference to the accompanying drawings in which.

DETAILED DESCRIPTION

In the drawings, reference numeral 10 generally designates an embodiment of a catheter assembly. The catheter assembly 10 includes a handle assembly 12. A catheter sheath 14 extends from a distal part 16 of the handle assembly 12. The catheter sheath 14 defines a plurality of lumens 18, 20 and 22(FIG. 4). The lumen 18 is a deflection stylet lumen for receiving a deflection stylet 24. The lumen 20 is a conductor lumen and has a plurality of conductors 26 (including thermocouple conductors) received therein. The conductors 26 extend from electrodes carried on a distal part 30 (see FIG. 3) of the catheter sheath toward the proximal end of the catheter sheath 14. The conductors 26 further extend through the handle 12 to an electrical connector 32(FIG. 1) arranged at a proximal end 34 of the handle assembly 12. The catheter sheath 14 is releasably connected to the distal part 16 of the handle assembly 12. The catheter sheath 14 and the handle assembly 12 each comprise suitable connectors (not shown in detail) for connecting the conductors from the catheter sheath 14 to the distal end 16 of the catheter handle assembly 12. The stylet is arranged to fit through the connectors of the catheter sheath 14 and the distal end 16 of the handle into the deflection stylet lumen 18.

Figure 1:
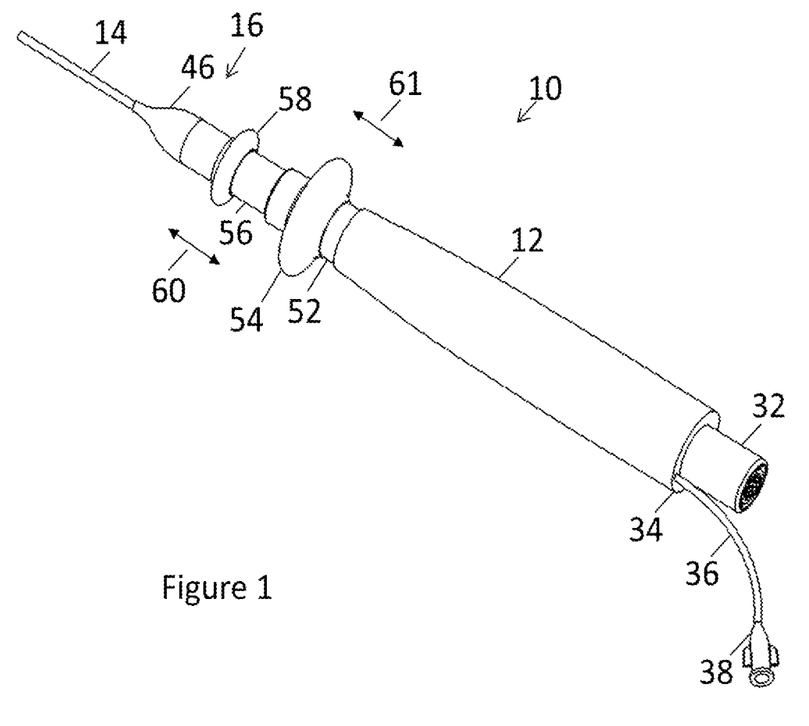
FIG. 1 shows a perspective view of an embodiment of a catheter assembly.

The lumen 22 is an irrigation lumen for providing irrigating fluid to the electrodes at the distal part 30 of the catheter sheath 14. The lumen 22 communicates with a fluid conduit 36(FIG. 1). A luer connector 38 is arranged at a proximal end of the conduit 36 for connection to a supply of irrigation fluid (not shown).

Figure 2:
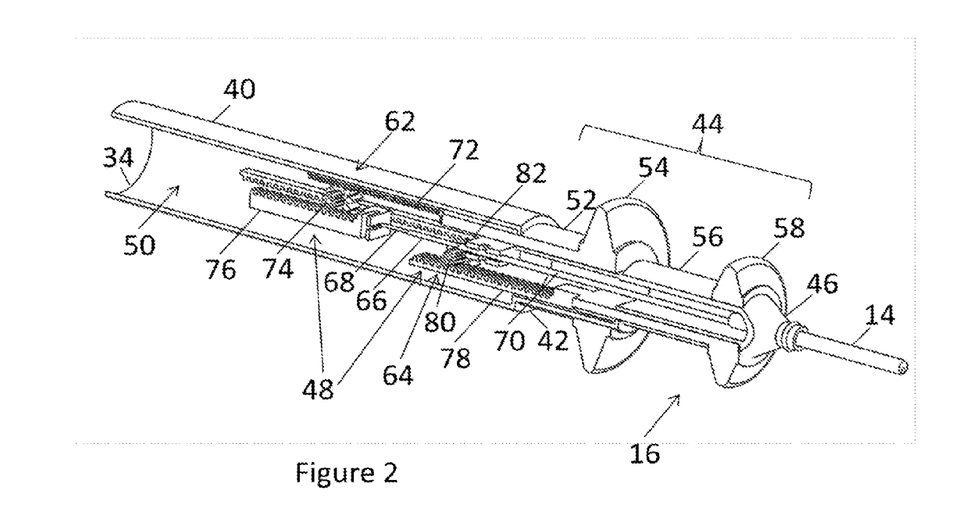
FIG. 2 shows a schematic, perspective, sectional view of a part of the catheter assembly.

An embodiment of the handle assembly 12 is now described in greater detail with reference to FIG. 2 of the drawings.

The handle assembly 12 includes a tubular handle body 40 defining the proximal end 34 to which the connector 32 (FIG. 1) is integrated and a distal end 42. A carrier arrangement 44 projects from the distal end 42 of the handle body 40. The carrier arrangement 44 mounts the catheter sheath 14, via a strain relief unit 46, and at least a part of a proximal region of the deflection stylet 24, as will be described in greater detail below. An adjustment unit 48 is arranged in a passage 50 of the handle body 40.

The carrier unit 44 comprises a deflection unit in the form of a first tubular member or tube 52 having a control knob 54 arranged at a distal end of the tube 52. The carrier arrangement 44 further comprises a size selector unit in the form of a second tubular member or tube 56. Once again, the second tube 56 carries a control knob 58 at a distal end of the tube 56. The tubes 52 and 56 are telescopically arranged with respect to each other and with respect to the distal end 42 of the handle body 40. Thus, the tubes 52 and 56 can be slid axially with respect to each other, and independently of each other, in the direction of arrows 60 and 61 (FIG. 1) as will be described in greater detail below.

The adjustment unit 48 comprises a first gear mechanism 62 associated with the tube 52 and a second gear mechanism 64 associated with the second tube 56. The deflection stylet 24 comprises a tubular member 66 having a bend-enhancing portion (not shown) proximate its distal end. An actuator 68, which may be in the form of a wire, is received in the tubular member 66 and a distal end of the actuator 68 is fastened with a distal part of the tubular member 66, distally of the bend-enhancing portion of the tubular member 66. The bend-enhancing portion may comprise any suitable bend-enhancing region, which forms a zone of weakness at the distal part of the catheter to allow bending around the bend-enhancing portion. For example, the bend-enhancing portion could be groups of slots, a longitudinally extending scalloped region, or the like.

The stylet 24 further includes a size selector in the form of a sleeve 70, which is displaceably arranged with respect to the tubular member 66 of the stylet 24 for interacting with the bend-enhancing portion to increase or reduce the size of the bend-enhancing portion and, in so doing, to control the degree of curvature of the distal part 30 of the catheter sheath 14 (in which the stylet 24 is received). This is shown in greater detail in FIG. 3 of the drawings indicating size selectability or the extent of deflection of the distal part 30 of the catheter sheath 14.

The sleeve 70 is, in the illustrated embodiment, shown as being mounted over the tubular member 66. It will, however, be appreciated that the sleeve 70 could be received within the tubular member 66 so that it is interposed between the tubular member 66 and the actuator 68.

The first gear mechanism 62 comprises a drive gear in the form of a rack 72 extending proximally from a proximal end of the tube 52 of the carrier arrangement 44. The rack 72 cooperates with a driven gear assembly comprising a pinion 74 rotatably received in the passage 50 of the handle body 40 and a second rack 76 slidably arranged in the passage 50 of the handle body 40. The rack 76 mounts a proximal end of the actuator 68. The tubular member 66 of the stylet 24 is anchored within the handle body 40. Thus, by displacing the deflector unit of first tubular member 52 and control knob 54 in the direction of arrows 61(FIG. 1), relative movement between the tubular member 66 and the actuator 68 occurs, resulting in deflection of the distal part 30 of the catheter sheath 14. As illustrated, the distal part 30 can deflect in the direction illustrated in FIG. 3 of the drawings or, by appropriate manipulation of the deflector unit of first tubular member 52 and control knob 54 in the opposite direction of the longitudinal axis of the catheter sheath but within the plane of the page in which FIG. 3 lies. The in-plane deflection is enhanced by having the stylet lumen 18 eccentrically arranged within the catheter sheath 14.

Figure 3:
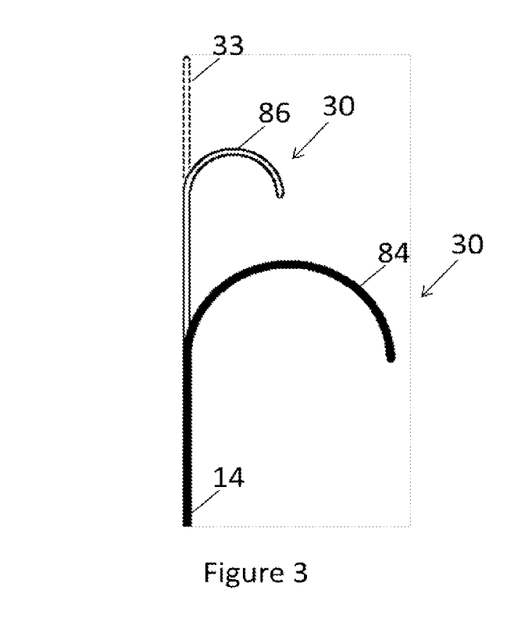
FIG. 3 shows a schematic view of a range of adjustability of a catheter sheath of the catheter assembly.
Figure 4:
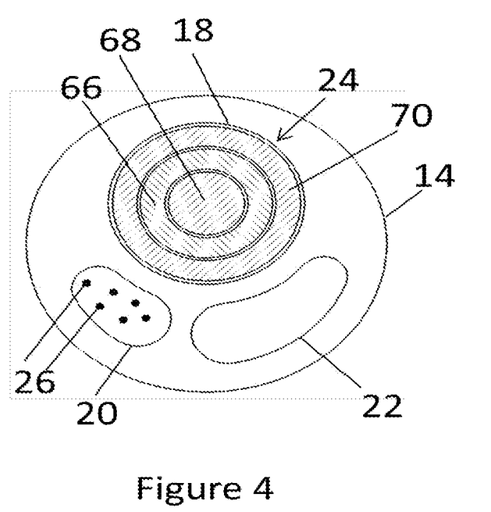
FIG. 4 shows a cross-sectional view, on an enlarged scale, through a catheter sheath of the catheter assembly.

To facilitate the bi-directional deflection of the distal part 30 of the catheter sheath 14, when the deflector unit of first tubular member 52 is in a rest position, i.e., the position in which the distal part 30 extends longitudinally as shown by the dotted reference lead line of reference numeral 33 in FIG. 3 of the drawings, the pinion 74 is substantially centrally arranged on the racks 72 and 76, i.e., inwardly of ends of the racks 72 and 76. This allows push—pull movement of the actuator 68 in the direction of arrows 61 (FIG. 1) so that bi-directional deflection occurs.

The gear mechanism 64 associated with the size selector tube 56 comprises a second drive gear in the form of a rack 78 projecting proximally from a proximal end of the tube 56. Once again, the rack 78 cooperates with a driven gear assembly comprising a pinion 80 rotatably mounted in the passage 50 of the handle body 40 and a second rack 82 slidably arranged within the passage 50 of the handle body 40. The rack 82 mounts a proximal end of the size selector sleeve 70. Thus, by appropriate manipulation of the selector tube 56 in the direction of arrows 60 (FIG. 1), a different size of curvature of deflection of the distal part 30 of the catheter sheath 14 can be selected.

When the tube 56 is withdrawn proximally fully into the tube 52, the rack 78 drives the pinion 80 and driven rack 82 to urge the sleeve 70 into the stylet lumen 18 of the catheter sheath 14 to occlude a part of the bend-enhancing portion of the stylet 24, resulting in a tighter radius of curvature as shown at 86 in FIG. 3 of the drawings. Conversely, when the tube 56 is extended distally with respect to the tube 52, the rack 78 drives the pinion 80 and drive rack 82 to withdraw the sleeve 70 from the stylet lumen 18, exposing more of the bend-enhancing portion of the stylet 24 and allowing for a greater radius of curvature as shown at 84 in FIG. 3 of the drawings.

The handle body 40 is made up of mating parts so that the parts can be separated to enable access to be gained to the passage 50 of the handle body 40. The proximal end of the actuator 68 is releasably attached to the rack 76 and the tubular member 66 of the stylet 24 is, likewise, releasably mounted in the passage 50 of the handle body 40. The releasable connection is preferably arranged by molding a slot or another similar receiving formation on the rack 76 where the proximal end of the actuator 68 can be securely fitted. Likewise, the handle body 40 comprises a slot or another suitable receiving formation molded in the passage 50 for securely but releasably fitting the proximal end of the tubular member 66 of the stylet 24 into the handle body. The proximal end of the actuator 68 and the proximal end of the tubular member 66 each have a mounting formation (not shown in figures) such as an enlarged fitting at the respective proximal ends. The mounting formation is a snug fit in the corresponding receiving formation in the rack 76 and the handle body 40. The sleeve 70 is attached in a similar fashion to the drive rack 82 having a suitable receiving formation for the sleeve 70. One or more screws may be used to ensure that each of the actuator 68, tubular member 66, and sleeve 70 are securely anchored while the catheter is in use.

In an alternative embodiment of the invention, the sleeve 70 is connected directly to the size selector tube 56 so that the adjustment unit only comprises one gear mechanism 62 for deflecting the distal end of the catheter sheath 14. In this embodiment, displacing the size selector tube 56 and control knob 58 in the direction of arrows 60 (FIG. 1) results in displacement of the sleeve 70 directly within the catheter sheath 14.

The handle body 40 can be opened by separating the mating parts, the component parts of the deflection stylet 24 disconnected from the adjustment unit 48 and the deflection stylet 24 removed. Similarly, the catheter sheath 14 is removably mounted to the distal end 16 of the handle assembly 12. The catheter sheath 14 can thus also be removed from the handle assembly 12. In this way, the component parts of the catheter assembly 10, comprising the handle assembly 12, the deflection stylet 24 and the catheter sheath 14 can be removed for reprocessing and/or replacement. It is envisaged that, in general, the handle assembly 12 and the deflection stylet 24 can be reprocessed between twenty and fifty times, whereas the catheter sheath 14 can be reprocessed for approximately five re-uses. In this regard, the term "reprocessing" (and derivatives) is to be understood in a broad sense to include reprocessing, remanufacturing, refurbishment, or the like.

Hence, it is an advantage of the disclosed embodiments that a modular catheter assembly 10 is shown that lends itself to reprocessing. It will be appreciated by those skilled in the art that using a catheter only once is a very expensive procedure as the costs of production of the catheter are significant. By reprocessing the catheter and using its constituent parts a number of times, a substantial reduction in costs for the institution and, as an end result, for the patient using the catheters, can be achieved.

It is a further advantage of the disclosed embodiments that a handle assembly 12 is disclosed having positive drive, i.e., the gear arrangement, for effecting deflection and size selection. Using a positive drive results in more accurate control over deflection and size selection and improved tactility for the clinician.

Reference throughout this specification to "one embodiment," "some embodiments" or "an embodiment" means that a particular feature, structure or characteristic described in connection with the embodiment is included in at least one embodiment of the present invention. Thus, appearances of the phrases "in one embodiment," "in some embodiments" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

As used herein, unless otherwise specified, the use of ordinal adjectives "first," "second," "third," etc., to describe a common object, merely indicate that different instances of like objects are referred to, and are not intended to imply that the objects so described must be in a given sequence, either temporally, spatially, in ranking, or in any other manner.

In the claims below and the description herein, any one of the terms "comprising," "comprised of," or "which comprises" is an open term that means including at least the elements/features that follow, but not excluding others. Thus, the term "comprising," when used in the claims, should not be interpreted as being limitative to the means or elements or steps listed thereafter. For example, the scope of the expression "a device comprising A and B" should not be limited to devices consisting only of elements A and B. Any one of the terms "including," "which includes," or "that includes," as used herein, is also an open term that also means including at least the elements/features that follow the term, but not excluding others. Thus, "including" is synonymous with and means "comprising."

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some, but not other, features included in other embodiments, combinations of features of different embodiments are meant to be within the scope of the invention, and form different embodiments, as would be understood by those skilled in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Similarly, it is to be noticed that the term "coupled," when used in the claims, should not be interpreted as being limited to direct connections only. The terms "coupled" and "connected," along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B which may be a path including other devices or means. "Coupled" may mean that two or more elements are either in direct physical or electrical contact, or that two or more elements are not in direct contact with each other but yet still cooperate or interact with each other.

Thus, while there has been described what are believed to be the preferred embodiments of the invention, those skilled in the art will recognize that other and further modifications may be made thereto without departing from the spirit of the invention, and it is intended to claim all such changes and modifications as falling within the scope of the invention. For example, any formulas given above are merely representative of procedures that may be used. Functionality may be added or deleted from the block diagrams and operations may be interchanged among functional blocks. Steps may be added or deleted to methods described within the scope of the invention.

It will be appreciated by persons skilled in the art that numerous variations and/or modifications may be made to the disclosure as shown in the specific embodiments without departing from the scope of the disclosure as broadly described. The present embodiments are, therefore, to be considered in all respects as illustrative and not restrictive.

The claims defining the invention are as follows:

1. A catheter handle assembly, comprising:
   a handle body having a proximal end and a distal end with a passage extending between the proximal end and the distal end of the handle body;
   a carrier arrangement projecting from the distal end of the handle body, the carrier arrangement configured for mounting a catheter sheath and at least a part of a deflection stylet of a catheter thereto during use of the catheter handle assembly; and
   an adjustment unit interposed between the handle body and the carrier arrangement, the adjustment unit comprising a gear mechanism that acts on the deflection stylet for adjusting deflection of a distal part of the stylet and the extent of deflection of the distal part of the stylet.

2. The assembly of claim 1, wherein the carrier arrangement comprises a deflection unit and a size selector unit.

3. The assembly of claim 2, wherein the deflection unit comprises a first tube and the size selector unit comprises a second tube with the first tube and the second tube being telescopically arranged with respect to each other and with respect to the distal end of the handle body.

4. The assembly of claim 3, wherein the gear mechanism comprises a first drive gear element carried by the first tube and a second drive gear element carried by the second tube, the gear mechanism further comprising a first driven gear assembly arranged in the handle body to be driven by the first drive gear element to effect deflection of the distal part of the stylet and a second driven gear assembly arranged in the handle body to be driven by the second drive gear element to effect selection of the size of the deflection of the stylet.

5. The assembly of claim 4, wherein each of the first drive gear element and the second drive gear element comprises a rack.

6. The assembly of claim 5, wherein each rack projects proximally from a proximal end of its associated tube.

7. The assembly of claim 5, wherein each of the first driven gear assembly and the second driven gear assembly comprises a driven gear and a secondary rack.

8. The assembly of claim 7, wherein each secondary rack carries a mounting formation for removably mounting a part of the stylet.

9. The assembly of claim 7, wherein the driven gear of the first driven gear assembly is located inwardly of ends of its associated rack when the distal part of the stylet is in a non-deflected condition, in use, so that bidirectional deflection of the distal part of the stylet is able to be effected by appropriate manipulation of the deflection unit.

10. The assembly of claim 1, wherein the handle body comprises a number of parts that are mated together to form the handle body, the parts being separable from each other to enable access to be gained to an interior of the handle body.

11. A catheter assembly comprising:
    a catheter handle assembly, comprising:
       a handle body having a proximal end and a distal end with a passage extending between the proximal end and the distal end of the handle body;
       a carrier arrangement projecting from the distal end of the handle body, the carrier arrangement configured for mounting a catheter sheath and at least a part of a deflection stylet of a catheter thereto during use of the catheter handle assembly; and
       an adjustment unit interposed between the handle body and the carrier arrangement, the adjustment unit comprising a gear mechanism that acts on the deflection stylet for adjusting deflection of a distal part of the stylet and the extent of deflection of the distal part of the stylet;
    a catheter sheath extending from the distal end of the handle body, the catheter sheath defining at least one lumen; and
    a deflection stylet extending from the handle body and received in the at least one lumen of the catheter sheath.

12. The catheter assembly of claim 11, wherein the carrier arrangement comprises a deflection unit and a size selector unit.

13. The catheter assembly of claim 12, wherein the deflection unit comprises a first tube and the size selector unit comprises a second tube with the first tube and the second tube being telescopically arranged with respect to each other and with respect to the distal end of the handle body.

14. The catheter assembly of claim 13, wherein the gear mechanism comprises a first drive gear element carried by the first tube and a second drive gear element carried by the second tube, the gear mechanism further comprising a first driven gear assembly arranged in the handle body to be driven by the first drive gear element to effect deflection of the distal part of the stylet and a second driven gear assembly arranged in the handle body to be driven by the second drive gear element to effect selection of the size of the deflection of the stylet.

15. The catheter assembly of claim 14, wherein each of the first drive gear element and the second drive gear element comprises a rack.

16. The catheter assembly of claim 15, wherein each of the first driven gear assembly and the second driven gear assembly comprises a driven gear and a secondary rack.

17. The catheter assembly of claim 16, wherein each secondary rack carries a mounting formation for removably mounting a part of the stylet.

18. The catheter assembly of claim 17, wherein the driven gear of the first driven gear assembly is located inwardly of ends of its associated rack when the distal part of the stylet is in a non-deflected condition, in use, so that bidirectional deflection of the distal part of the stylet is able to be effected by appropriate manipulation of the deflection unit.

\* \* \* \* \*

UNITED STATES PATENT AND TRADEMARK OFFICE
CERTIFICATE OF CORRECTION

PATENT NO. : 9,254,372 B2  
APPLICATION NO. : 13/816711  
DATED : February 9, 2016  
INVENTOR(S) : Garrett Ryan

Page 1 of 1

It is certified that error appears in the above-identified patent and that said Letters Patent is hereby corrected as shown below:

In the specification:

| | | |
|---|---|---|
| COLUMN 1, | LINE 11, | change "Al on Feb. 16," to --A1 on Feb. 16,-- |
| COLUMN 3, | LINE 13, | change "22(FIG. 4)." to --22 (FIG. 4).-- |
| COLUMN 3, | LINE 18, | change "sheath toward" to --sheath 14 toward-- |
| COLUMN 3, | LINE 20, | change "connector 32(FIG. 1)" to --connector 32 (FIG. 1)-- |
| COLUMN 3, | LINE 33, | change "36(FIG. 1)." to --36 (FIG. 1).-- |
| COLUMN 4, | LINE 33, | change "arrows 61(FIG. 1)." to --arrows 61 (FIG. 1).-- |
| COLUMN 7, | LINE 10, | change "ofB which" to --of B, which-- |

Signed and Sealed this  
Twenty-fourth Day of May, 2016

Michelle K. Lee  
*Director of the United States Patent and Trademark Office*